(12) United States Patent
Wilen

(10) Patent No.: US 8,225,817 B2
(45) Date of Patent: Jul. 24, 2012

(54) FLOW DISTRIBUTING VALVE

(75) Inventor: Anders Wilen, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 451 days.

(21) Appl. No.: 12/597,826

(22) PCT Filed: Apr. 24, 2008

(86) PCT No.: PCT/SE2008/000288
§ 371 (c)(1),
(2), (4) Date: Oct. 27, 2009

(87) PCT Pub. No.: WO2008/140374
PCT Pub. Date: Nov. 20, 2008

(65) Prior Publication Data
US 2010/0058841 A1    Mar. 11, 2010

(30) Foreign Application Priority Data

May 15, 2007 (SE) ....................... 0701221

(51) Int. Cl.
*F16K 11/074* (2006.01)
*G01N 1/00* (2006.01)
(52) U.S. Cl. .................. 137/625.18; 73/863.72

(58) Field of Classification Search .................. None
See application file for complete search history.

(56) References Cited

U.S. PATENT DOCUMENTS

| 3,411,525 A | * | 11/1968 | Auger ........................... 137/270 |
| 4,444,066 A | * | 4/1984 | Ogle et al. ................. 73/863.72 |
| 4,506,558 A | * | 3/1985 | Bakalyar .................... 73/863.72 |
| 4,614,204 A | | 9/1986 | Dolejs |
| 4,625,569 A | * | 12/1986 | Toei et al. ................... 73/863.72 |
| 5,207,109 A | * | 5/1993 | Olsen .......................... 73/863.73 |
| 5,803,117 A | * | 9/1998 | Olsen et al. ............... 137/625.15 |
| 6,012,488 A | | 1/2000 | Nichols |
| 6,155,123 A | * | 12/2000 | Bakalyar .................... 73/864.83 |
| 6,672,336 B2 | * | 1/2004 | Nichols .................... 137/625.46 |

FOREIGN PATENT DOCUMENTS

GB    1 263 481    2/1972
* cited by examiner

*Primary Examiner* — John Fox

(57) ABSTRACT

A rotary valve (10) for distributing a flow of a fluid is provided, the valve comprising a stator (11) and a rotor (12). Furthermore a chromatography system, comprising such a rotary valve and three different components or component groups connected to the valve is provided. With this rotary valve according to the invention the flow direction is kept constant through one of the three components or component groups while the flow direction through the other two component or component groups can be changed.

5 Claims, 11 Drawing Sheets

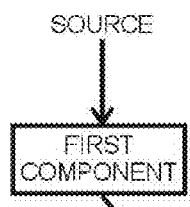
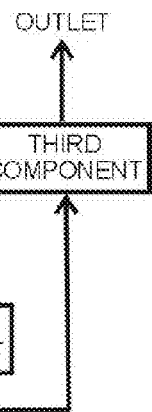
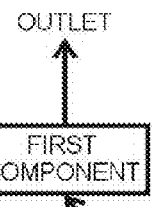
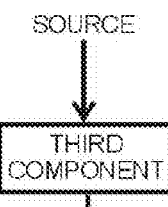
Fig. 1
Fig. 2
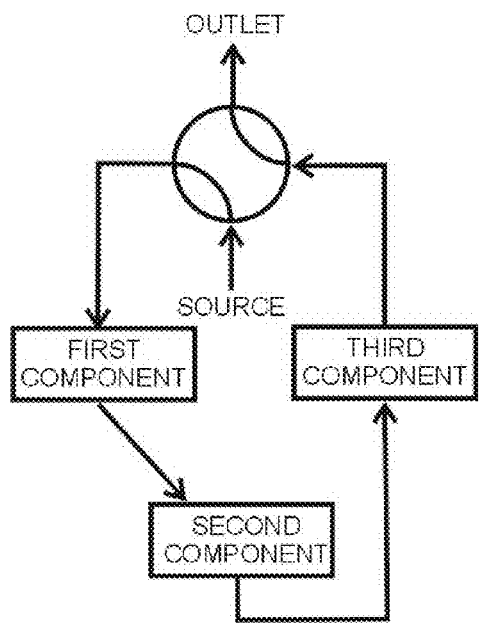
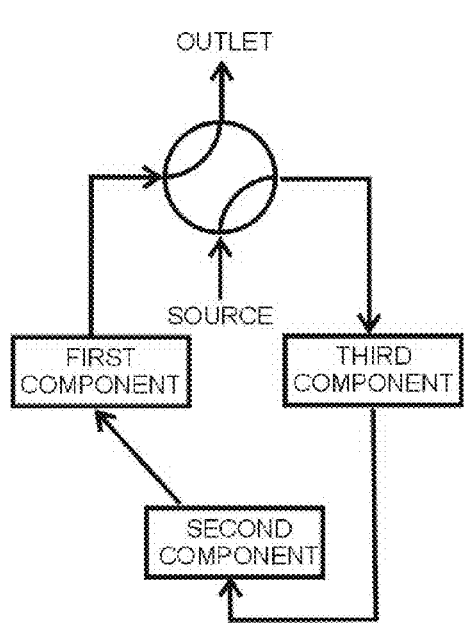
Fig. 3
Fig. 4

FLOW DISTRIBUTING VALVE

CROSS-REFERENCE TO RELATED APPLICATIONS

This application is a filing under 35 U.S.C. §371 and claims priority to international patent application number PCT/SE2008/000288 filed Apr. 24, 2008, published on Nov. 20, 2008, as WO 2008/140374, which claims priority to patent application number 0701221-4 filed in Sweden on May 15, 2007.

FIELD OF THE INVENTION

The present invention relates to valves and more specifically to rotary valves used to direct the flow of a fluid in a flow-distributing instrument, such as a liquid chromatography system.

BACKGROUND OF THE INVENTION

Valves are commonly used in devices that involve the transportation of a fluid. A typical use is to direct the fluid into one of a multitude of possible flow paths. For instance, in the field of liquid chromatography systems for laboratory use, where flow paths typically are of an inner diameter in the range of 0.25-2 mm, two-way solenoid valves are often used to direct a fluid. Examples of such valves are valves of the MTV series available from TAKASAGO Electrical Inc., Nagoya, Japan.

Solenoid valves tend to have limitations when used in applications where the fluid pressure is relatively high (such as pressures above approximately 0.5 MPa).

In addition, they are not well suited as multi flow path valves, i.e. valves with more than one inlet/outlet used at the same time.

For such applications, the use of rotary valves is well known in the art. Generally, a rotary valve has a stationary body, herein called a stator, which co-operates with a rotating body, herein called a rotor.

The stator is provided with a number of inlet and outlet ports. The ports are via bores in fluid communication with a corresponding set of orifices on an inner stator face. The inner stator face is an inner surface of the stator that is in fluid tight contact with an inner rotor face of the rotor. The rotor is typically formed as a disc and the inner rotor face is pressed against the inner stator face in rotating co-operation. The inner rotor face is provided with one or more grooves which interconnect different orifices depending on the rotary position of the rotator with respect to the stator.

Rotary valves can be designed to withstand high pressures (such as pressures above 30 MPa). They can be made from a range of materials, such as stainless steel, high performance polymeric materials and ceramics.

The number of inlets/outlets as well as the design of grooves in the rotator or the stator reflects the intended use of a specific valve.

A common type of multi-purpose valve has one inlet port (typically placed in the rotary axis of the valve) and a number of outlets ports that are placed equidistantly around the inlet port. The rotor has a single, radially extending groove that has one end in the rotary centre, thereby always connecting to the inlet, while the other end connects to any one of the outlets depending on the angular position of the rotor with respect to the stator. Such a valve is useful to direct a flow from the inlet to any of the outlets—one at a time.

More complicated arrangements are possible. For instance, it may be beneficial to allow more than one fluid to pass a valve or to allow a flow to pass the same valve more than one time. Valves have been designed that solves various situations of this kind.

An example of such a valve is the dual random access, three-way rotary valve that is described in U.S. Pat. No. 6,672,336, issued to Nichols. This valve solves the problem of allowing a first fluid to be directed either to an outlet "A" or an outlet "B", and a second fluid to be directed either to an outlet "C" or an outlet "D", all implemented in a single valve that permits the direction of the first fluid to be independent of the direction of the second fluid.

Another situation that may need to be solved for a flow-distributing system is when a flow shall be directed via three components in an alternating way, as illustrated in FIGS. 1 and 2.

The first component, the second component and the third component represents any components (or set of components) through which the flow should be guided, such as sensors, chromatography columns, other valves etc.

Provided that the flow direction through each component is of no importance (or is actually intended to be switched), this situation is easily solved with a conventional 4-way double-path valve, schematically shown in FIGS. 3 and 4.

However, the solution of FIGS. 3 and 4 is not useful in a case where the flow direction through one of the components—the second component in the figures—must not be altered. That situation is schematically illustrated in FIGS. 5 (which is similar to FIG. 1) and 6.

Examples (taken from the field of liquid chromatography) of components for which the flow direction is of importance, i.e. components that have different properties or different influence on the fluid depending on the flow direction, are sensors with non-symmetrical inner chambers, chromatography columns, ball valves etc.

Therefore, there is a need for a single valve that, in a first position, directs a flow:

from a source, through a first component, through a second component, through a third component and out through an outlet, and in a second position directs the flow:

from the source, through the third component, through the second component, through the first component and out of the outlet, while allowing the flow to pass the second component in the same flow direction in both of said first and second positions.

BRIEF DESCRIPTION OF THE INVENTION

This need is solved with a flow distributing valve according to claim 1 of the present application.

Furthermore, according to a second aspect of the present invention, a chromatography system according to claim 4 is described, said chromatography system comprising a valve according to claim 1.

BRIEF DESCRIPTION OF THE DRAWINGS

FIG. 1 is a schematic view of flow through three components in a first mode.

FIG. 2 is a schematic view of flow through three components in a second mode.

FIG. 3 is a schematic view of flow through three components using a conventional valve in a first mode.

FIG. 4 is a schematic view of flow through three components using a conventional valve in a second mode.

DETAILED DESCRIPTION OF THE INVENTION

Figures 5, 6:
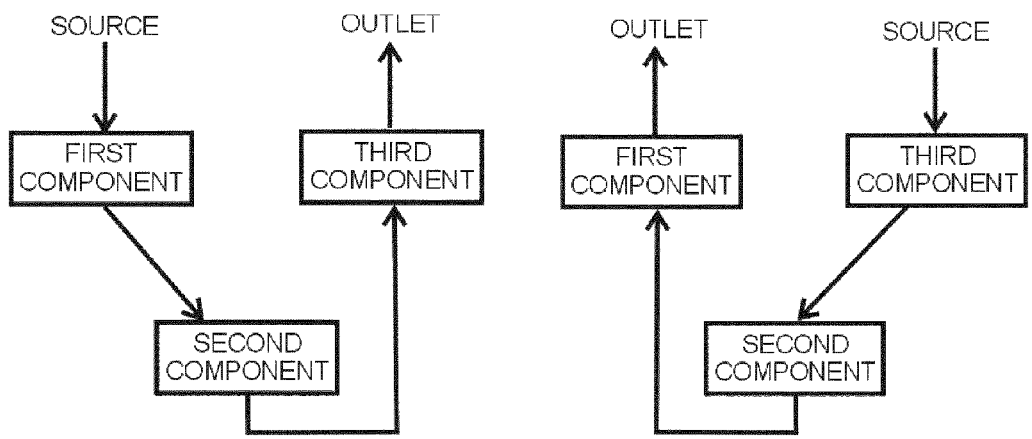
FIG. 5 is a schematic view of flow through three components in a first mode.
FIG. 6 is a schematic view of flow through three components in a second mode.
Figure 7:
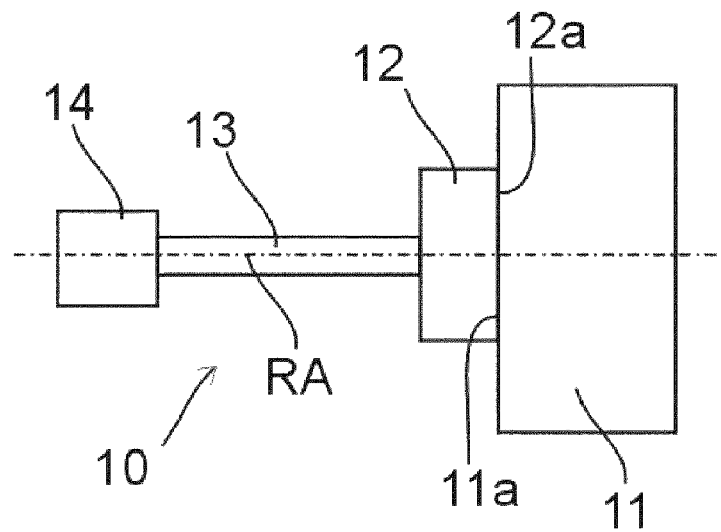
FIG. 7 is a schematic side view of a rotary valve.

The main parts of a typical rotary valve are schematically shown in FIG. 7 (wherein no brackets or similar load carrying or fastening elements are shown). The rotary valve 10 has a stator 11, a rotor 12, a rotary shaft 13 that optionally may be provided with means (not shown) for recognizing its angular position and a driving unit 14 typically comprising a gear box and a motor (although a valve also may be operated manually). The rotor is rotatable with respect to the stator around a rotary axis RA of the valve.

The stator 11, which is fixed with respect to the instrument into which it is built, is provided with ports (not shown in FIG. 7) for fluid communication with a fluid source and any components with which the valve is to co-operate. The ports may be positioned on any suitable part of the stator, and in any suitable direction. The ports are provided with means to connect capillaries or tubing. Such means may be of any suitable type, such as conventional Valco fittings well known to anyone skilled in the art. The ports are via channels in fluid communication with a corresponding set of orifices on an inner stator face 11a, i.e. that surface of the stator that during operation is in contact with the rotor 12.

The rotor 12 is typically formed as a disc and has an inner rotor face 12a that is that face that is pressed against the inner stator face 11a during operation. The inner rotor face 12a is provided with one or more grooves which interconnect different orifices of the inner stator face 11a depending on the rotor position of the rotor with respect to the stator.

Figure 8:
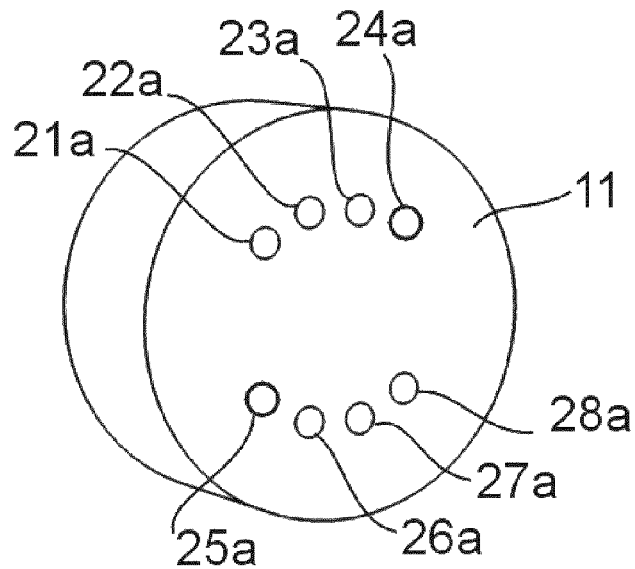
FIG. 8 is a schematic view of the inlets/outlets to/from a valve according to one embodiment of the present invention.

FIG. 8, which shows a simplified perspective view of a stator 11 of a flow distributing valve according to one embodiment of the invention, illustrates the inlet and outlet port arrangement of the valve. When explaining the use of the ports the terms "upper" and "lower" are used herein. These terms refer to the figures only, since the valve function is not dependent on how it is turned or positioned. However, the mutual positions of the ports (or more correctly the mutual positions of the orifices that connects the ports with the rotor) are of importance. Thus, the stator 11 according to one embodiment of the present invention has eight external ports, a first port 21a, a second port 22a, a third port 23a, a fourth port 24a, a fifth port 25a, a sixth port 26a, a seventh port 27a and an eighth port 28a that are used to connect the valve to all desired peripheral components.

Note that herein the term "component" may designate a single device, such as a chromatography column, or a set of interconnected devices, such as a number of in-line valves and monitors or even simply a piece of interconnecting tubing.

Figure 9:
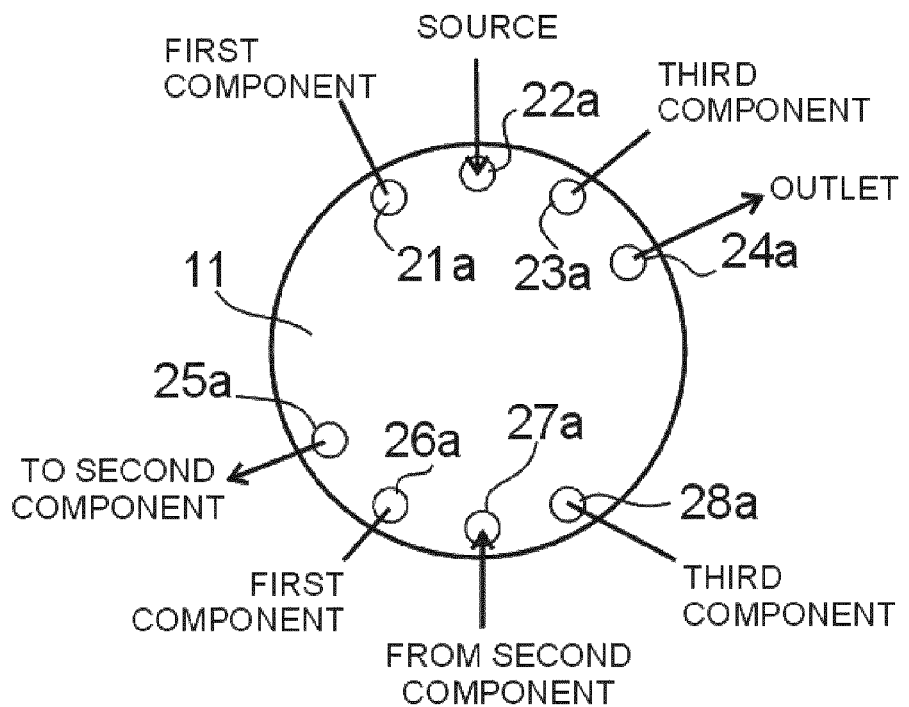
FIG. 9 is a schematic front view of the stator illustrated in FIG. 8.

FIG. 9 is a front view of the stator 11 according to the embodiment shown in FIG. 8, defining how the valve is connected to peripheral components. Fluid enters into the second port 22a from a source, such as a pump. A first component, which may be a valve, a monitor cell, a retaining capillary loop or any other useful component having an inlet and an outlet, is connected to the valve via the first and sixth ports 21a and 26a. Similarly, a third component is connected to the valve via the third and eighth ports 23a and 28a. The fifth port 25a is connected to the inlet of a second component, and the seventh port 27a receives the outlet flow from the second component. Finally, the fourth port 24a is an outlet port from which the fluid exits the valve (to any further components, receptacles or to waste).

Note that the ports associated with the first component will act alternately as inlets/outlets depending on the rotor position of the valve. The same is valid for the ports associated with the third component, while the fifth port 25a always is an outlet port to the second component and the seventh port 27a is always an inlet port from the second component. Note also that each port is connected to the inner stator face 11a via a channel. Each port will be connected to an orifice, i.e. a first orifice 21b is connected to the first port 21a, a second orifice 22b is connected to the second port 22a, a third orifice 23b is connected to the third port 23a, a fourth orifice 24b is connected to the fourth port 24a, a fifth orifice 25b is connected to the fifth port 25a, a sixth orifice 26b is connected to the sixth port 26a, a seventh orifice 27b is connected to the seventh port 27a and an eighth orifice 28b is connected to the eighth port 28a. Although not evident from the figures, the channel and its orifice on the inner stator face is typically of smaller diameter than the port in itself.

Figure 10:
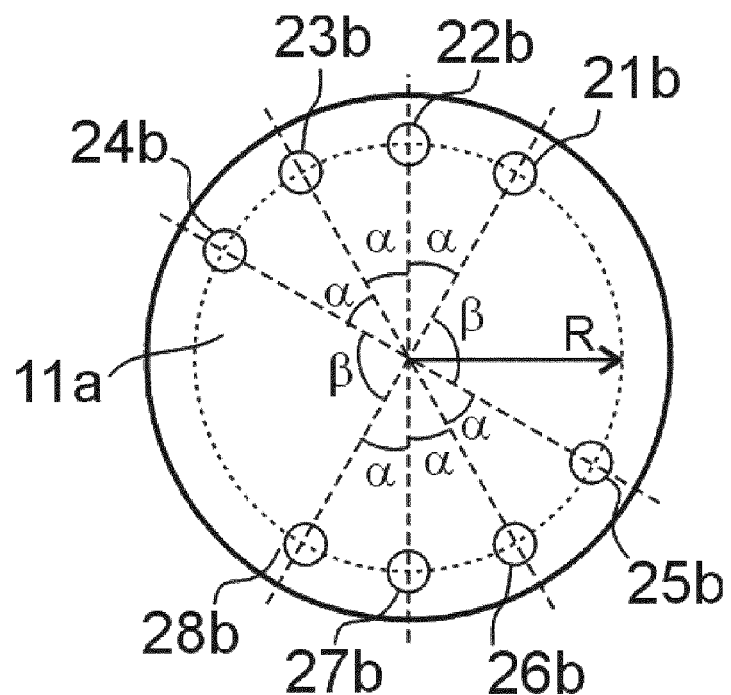
FIG. 10 shows schematically the angular distribution of the orifices of the inner stator face of the stator illustrated in FIGS. 8 and 9.
Figure 13:
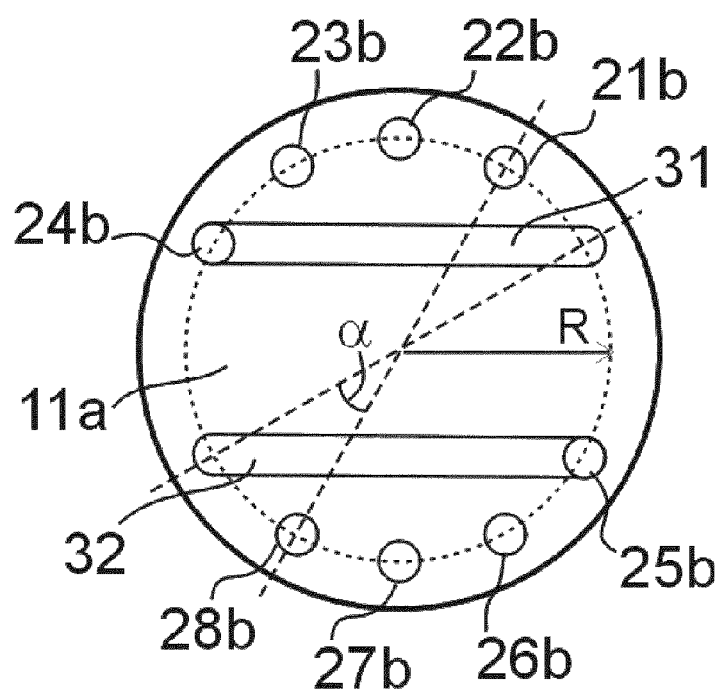
FIG. 13 is a schematic view of the inner stator face shown in FIG. 11, also showing the position of the groove ends.

Looking at the inner stator face 11a, the general angular distribution of the orifices is illustrated in FIG. 10 (note that for clarity reasons any stator grooves, as will be described later with reference to FIG. 13, are omitted from this figure). The position of the orifices in this embodiment of the invention can be described as grouped into two groups, one upper group comprising the first, the second, the third and the fourth orifices 21b-24b and lower group comprising the fifth, the sixth, the seventh and the eighth orifices 25b-28b. The individual upper orifices 21b-24b (corresponding to the ports 21a-24a) are equally parted by an angle α, as is the individual lower orifices 25b-28b (corresponding to the ports 25a-28a). The upper and lower groups of orifices, 21b-24b and 25b-28b respectively, are at each side parted with the same angle β. In a preferred embodiment, the angle α is 30°, while the angle β is 90°. However, other angles are possible, such as α=36° and β=72°. All orifices are of course placed with essentially the same radial distance R to the rotational axis of the valve.

Figure 11:
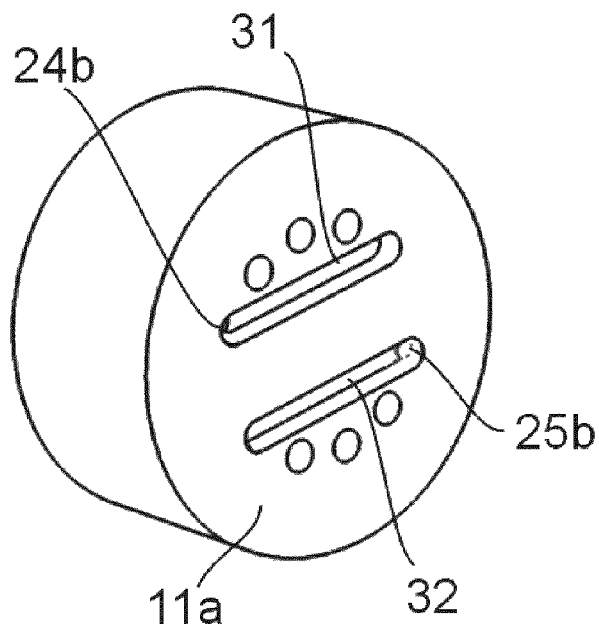
FIG. 11 is a schematic view of the stator of FIG. 8, showing the inner stator face.

In order to obtain the desired valve function, in addition to the orifices the inner stator face 11a is provided with a first stator groove 31 and a second stator groove 32, said grooves being essentially parallel to each other, as shown in FIG. 11 (not shown in FIG. 10). Note that one end of the first stator groove 31 connects to the fourth orifice 24b, i.e. it is in fluid communication with one end of the first component, while one end of the second stator groove 32 connects to the fifth orifice 25b, i.e. it is in fluid communication with one end of the third component.

Figure 12:
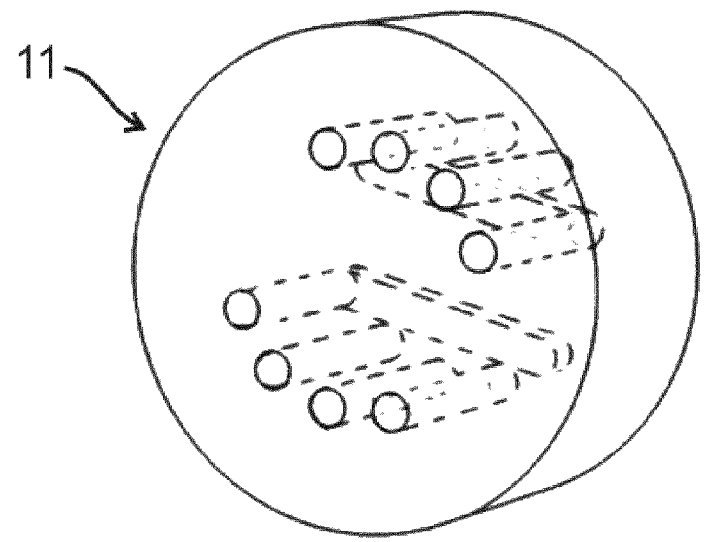
FIG. 12 is a perspective view of the stator shown in FIGS. 8-11 showing hidden orifices and channels.

This arrangement is also shown in FIG. 12 from the front side of the stator, with orifices and grooves indicated by broken lines.

Each stator groove 31, 32, which typically is of the same width as an orifice diameter, ends at a position that corresponds to an angular partition of the angle α from the nearest orifice, as illustrated in FIG. 13, and with the same radial distance R to the rotational axis of the valve as for the set of orifices.

Figure 14:
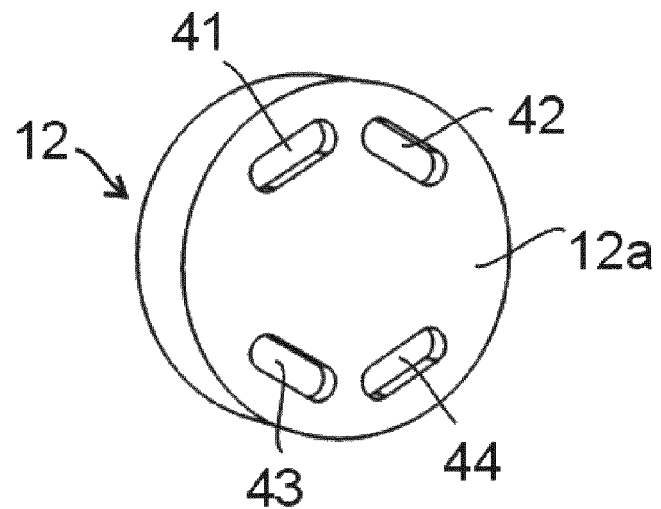
FIG. 14 is a schematic view of an inner rotor face of a rotor according to one embodiment of the invention. Said rotor is adapted to cooperate with a stator as shown in the FIGS. 8-13.
Figure 15:
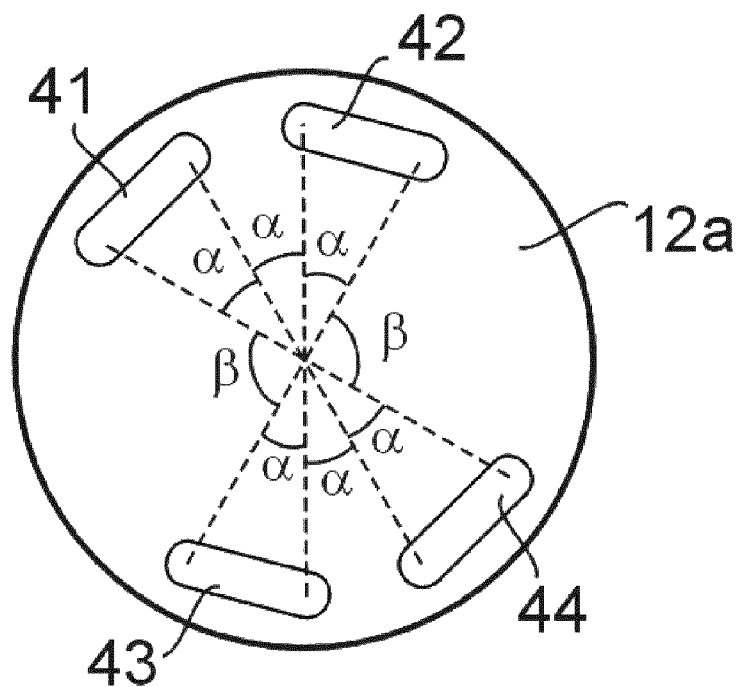
FIG. 15 shows schematically the angular distribution of the grooves of the rotor shown in FIG. 14.

The inner rotor face 12a of a rotor embodiment that is adapted to cooperate with the stator described above in relation to FIGS. 8-13 is shown in FIG. 14. It is provided with a first rotor groove 41, a second rotor groove 42, a third rotor groove 43 and a fourth rotor groove 44. The first and second rotor grooves 41, 42 being called upper rotor grooves and the third and fourth rotor grooves 43, 44 being called lower rotor grooves. The rotor grooves 41-44 are preferably of the same mutual size and shape, and are angularly distributed in a way that corresponds to the orifices of the stator 11 as shown in FIG. 15, i.e. the two upper rotor groove's 41, 42 closest ends are parted an angle α, the two lower rotor groove's 43, 44 closest ends are parted an angle α and the set of upper rotor grooves and the set of lower rotor grooves are parted an angle β in both directions. Each rotor groove (41-44) extends over the angle α dividing two adjacent orifices of the stator. At the same time, all ends of the rotor grooves 41-44 of the inner rotor face 12a are placed at essentially the same radial distance R from the centre of rotation as are the orifices of the inner stator face 11a.

When assembled, the inner rotor face 12a is pressed against the inner stator face 11a in a manner that is typical for any conventional rotary valve (which is well known for anyone skilled in the art, and will not be explained herein). The position of the rotor with respect to the valve stator of the present invention is such that two operative rotor positions are possible, as illustrated in FIGS. 16-19.

Figure 16:
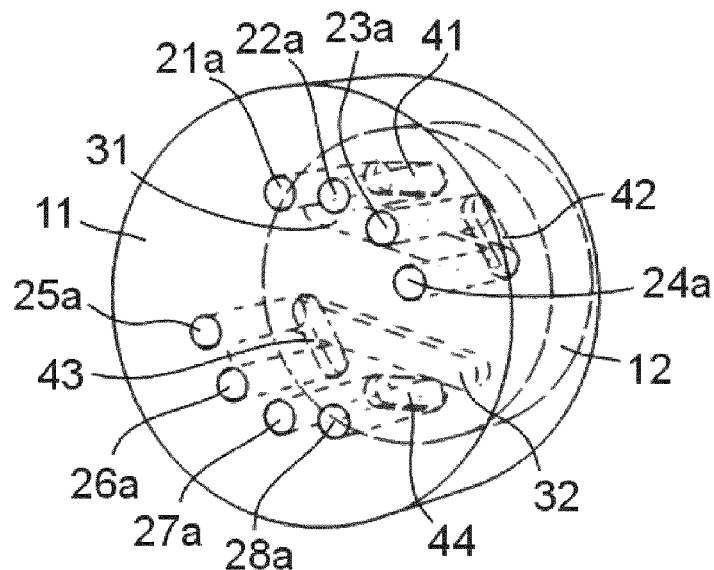
FIG. 16 is a perspective view of a first rotor position of the valve according to the embodiment of the invention shown in FIGS. 8-15.
Figure 17:
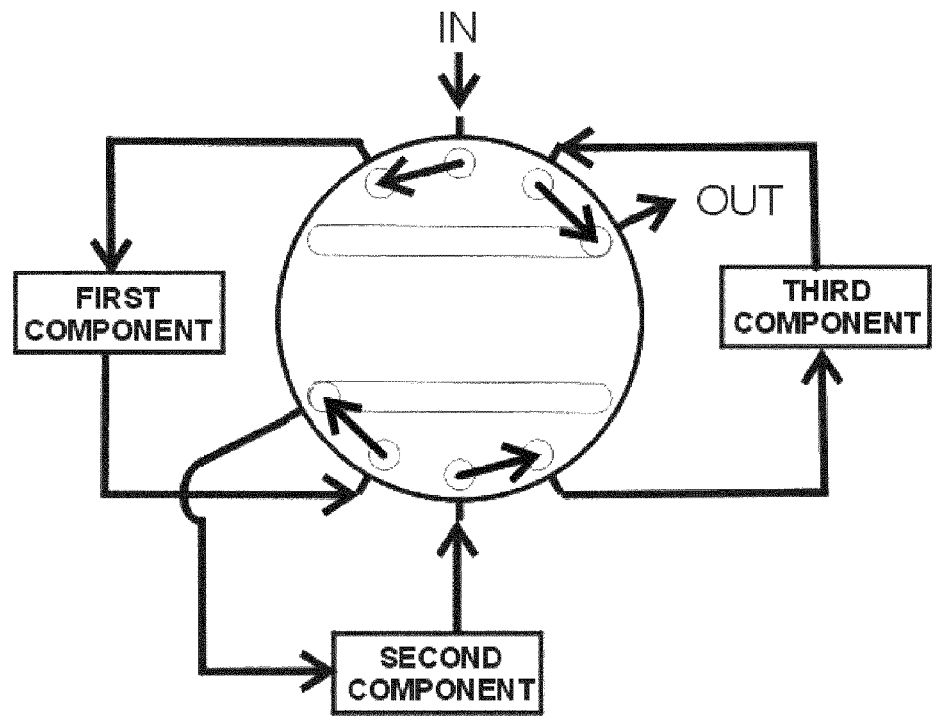
FIG. 17 is a schematic front view of the rotor position of the valve shown in FIG. 16.

In a first rotor position, as shown in FIGS. 16 and 17, the fluid enters the second port 22a, typically from a pump. The flow passes the first rotor groove 41, exits via the first port 21a to the first component and returns from the first component via the sixth port 26a. From there, the fluid passes the third rotor groove 43, and exits through the fifth port 25 to enter the second component. From the second component the fluid returns to the seventh port 27a of the valve, passes the fourth rotor groove 44 and exits via the eighth port 28a to the third component. From the third component the fluid returns to the third port 23a of the valve, passes the second rotor groove 42 and exits the valve via the fourth port 24a.

It should be noted that, although not described above, the fluid that passes any one of the ports 21a-28a of course also passes the corresponding orifice 21b-28b on the inner stator face. It should also be noted that in this rotor position the stator grooves 31 and 32 of the inner stator face 11a are not used except for the portion that connects to the fourth and fifth orifices 24b and 25b, respectively. Thus, they form cul-de-sacs that can be rinsed in the second rotor position, as described below.

Figure 18:
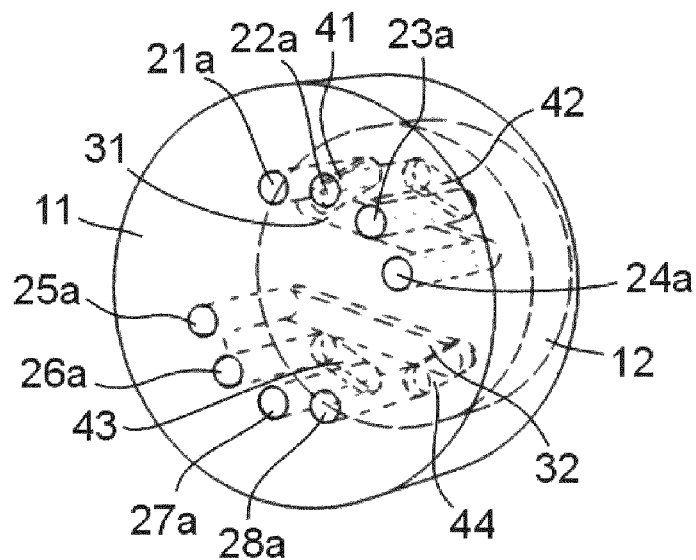
FIG. 18 is a perspective view of a second rotor position of the valve according to the embodiment of the invention shown in FIGS. 8-15.
Figure 19:
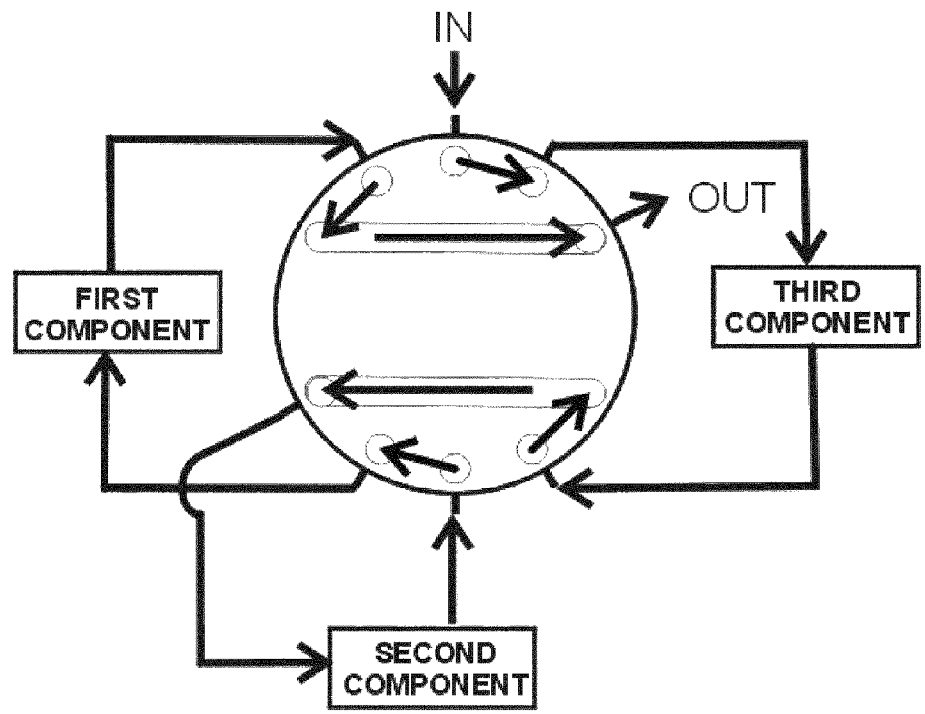
FIG. 19 is a schematic front view of the rotor position of the valve shown in FIG. 18.

A second rotor position, as shown in FIGS. 18 and 19, is in the illustrated embodiment obtained by rotating the rotor 12 the angle α counter-clockwise with respect to the stator 11 from the first position (when viewed from the stator front).

In the second rotor position the fluid enters the second port 22a in the same manner as for the first rotor position. The flow passes the second rotor groove 42 to exit via the third port 23a to the third component and returns from the third component via the seventh port 27a. The fluid then passes the fourth rotor groove 44, and then via the second stator groove 32 (which is then rinsed) to exit through the fifth port 25a to enter the second component. From the second component the fluid returns to the seventh port 27a of the valve, passes the third rotor groove 43 and exits via the sixth port 26a to the first component. From the first component the fluid returns to the first port 21a of the valve, passes the first rotor groove 41 and then via the first stator groove 31 (which is then rinsed) to exit the valve via the fourth port 24a.

A rotary valve according to the present invention allows the design of an advanced liquid chromatography system with a minimum of valve components. According to a second aspect of the invention a chromatography comprising a rotary valve as described above is provided.

An embodiment of such a liquid chromatography system shall now be described with reference to FIGS. 20 and 21, wherein the main components having relevancy to the present invention are illustrated while others, such as additional monitoring sensors, additional valves, regulating devices etc., although essential for the system as such are omitted for reasons of clarity.

Thus, the system includes a main liquid source such as a pump 302 that is connected to a flow distributing valve 301 according to the inventive valve described above. A sample injection valve 303 including an attached first sample retaining device, herein exemplified with a conventional capillary loop 311, is connected to the flow distributing valve as the first component (referring to the description of the flow distributing valve given above). A first selection valve 304 to which is connected a plurality (or at least one) of chromatography columns 312, 313 (for clarity reasons only two such columns 312, 313 are shown in the figure, the number of selectable columns being determined by the capacity of the first selection valve 304) is connected as the second component (referred to the description of the flow distributing valve above). In this embodiment the first selection valve is also connected in series with a sample monitoring device herein exemplified as a UV sensor 317 connected to a control unit (not shown) of the chromatography system and a flow path selection valve 305, whereby all these three components are referred to as the second component. A second selection valve 306 having a set of selectable sample retaining devices, herein exemplified with capillary loops 315, 316 (i.e. for clarity reasons only two such loops 315, 316 are shown in the figure, although the number of selectable loops is determined by the capacity of the selection valve 306), is connected to the flow distributing valve as the third component (referring to the description given above). Furthermore a collecting device 314, such as a conventional fraction collector, for collecting separated sample fractions is connected to the path selection valve 305. The components are interconnected with suitable tubing, such as PEEK capillaries having inner diameters adapted to the flow rate used in the system.

It is easily understood that the injection valve 303 with its attached components represents an example of "the first component" of the above description of the inventive flow distributing valve. Similarly, the second selection valve 306 with its attached loops represents an example of "the third component", while the first selection valve 304, columns 312 attached thereto, the UV sensor 317 and the flow path selection valve 305 together represents an example of "the second component" of the above description of the inventive flow distributing valve.

The sample injection valve 303 may be a conventional sample injection valve, such as the INV-907 injection valve available from GE Healthcare.

The injection valve 303 allows several operating positions. In a first, "INJECT" position a sample, such as a volume of liquid containing proteins and/or other components of biological origin, can be transferred to the first capillary loop 311, typically with a syringe connected to the injection valve 303. Typically, in this position the flow from the pump 302 passes through the injection valve 303 directly to the flow distributing valve 301 via the injection valve outlet. In a second, "LOAD" position the capillary loop is introduced into the flow between the pump 302 and the injection valve outlet. Thus, in the "LOAD" position the sample is forced out of the capillary loop 311 and into the flow distributing valve 301.

The first and second selection valves 304, 306 may both be conventional multi-purpose valves, as for example the 6-port ST valve available from Valco Instruments Co. Inc. One such valve placed before the columns/loops and one after the columns/loops.

The flow path selection valve 305 is typically a conventional multi-purpose valve of the type described in the prior art background of the present application.

Initially, a sample for purification is introduced into the capillary loop 311 of the injection valve 303 when the injection valve is in its INJECT position.

Figure 20:
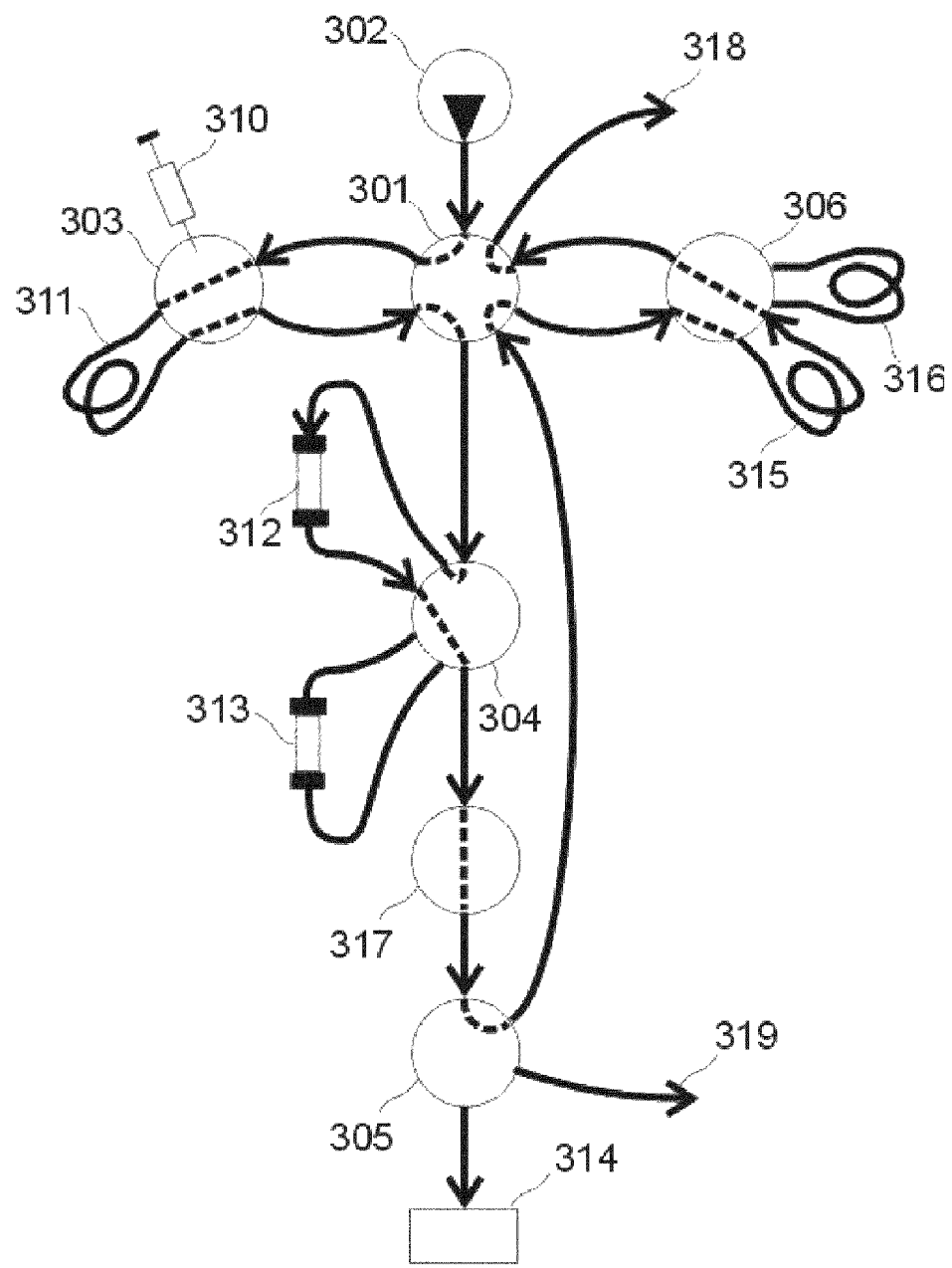
FIG. 20 is a schematic view of a chromatography system using a valve according to the invention, in a first operating mode.

Then, the chromatography system is set in a first operating mode illustrated in FIG. 20 characterized by that the flow distributing valve 301 is in a first position corresponding to the first rotor position shown in FIG. 17. Note that for clarity reasons the mutual positions of the inlets/outlets of valve 301 in FIG. 20 are not drawn identically to that of the embodiment shown in FIG. 17.

Further, in the first operating mode of the system the injection valve 303 is in its LOAD position, the first selection valve 304 is set to connect one of the columns 312 in-line, and the second selection valve 306 is set to connect one of the loops, e.g. loop 315 in-line.

With the pump 302 the buffer liquid used is forced through the flow distributing valve 301 to injection valve 303 where it brings the content of the loop 311 (the sample) to exit the injection valve 303 to the flow distributing valve 301. Via flow distributing valve 301 and the first selection valve 304 the sample is filled into the chromatography column 312. Depending on the chromatography technique used the sample is separated by the column into components, either directly or in a subsequent step using a different buffer liquid. In this illustrating description it is assumed that the separation occurs in one step although the invention is likewise useful for any chromatography technique.

The separated components are detected with the UV sensor 317. The UV signal is processed by the control unit (not shown) of the chromatography system and is used to control the position of the flow path selection valve 305. Thus, the flow path selection valve 305 may be set in a position where a detected sample fraction is collected with the fraction collector 314, or the liquid passing the flow path selection valve 305 may be directed to a waste outlet 319 (or any optional receptacle). However, a detected fraction may also be routed by the flow path selection valve 305 back to the flow distributing valve 301. From that valve it is directed to the second selection valve 306 to be contained in the selected loop 315. Any excess liquid is passed back to the flow distributing valve 301 to be expelled from the system via the outlet 318.

Thus, several different separated fractions can be isolated and selectively be placed in the fraction collector 314 or alternatively in different loops 315, 316 as selected by changing the setting of the second selection valve 306. This can all be controlled automatically via the control unit of the system based on analysis of the UV signal from the UV detector 317.

Figure 21:
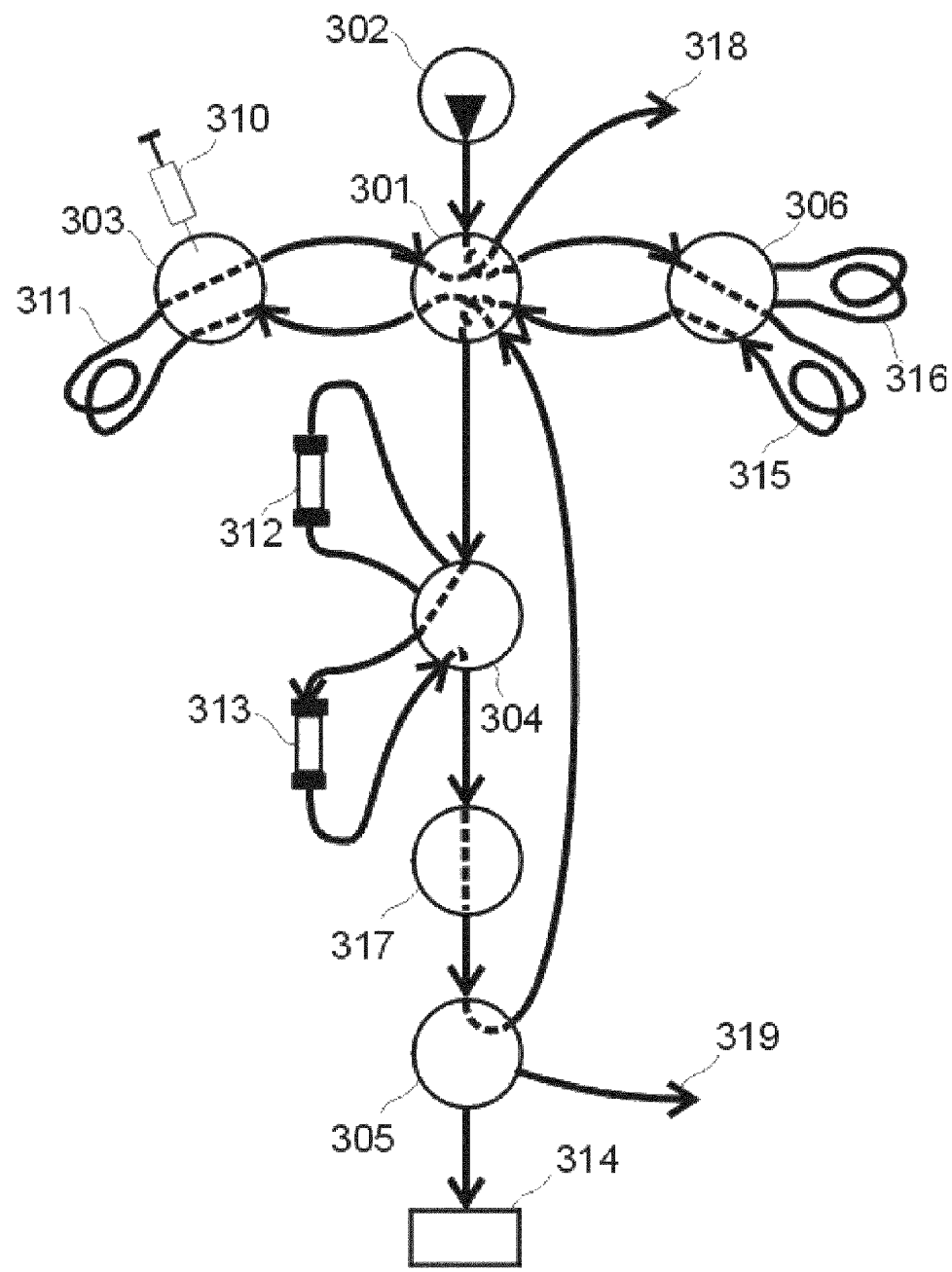
FIG. 21 is a schematic view of a chromatography system using a valve according to the invention, in a second operating mode.

A second operating mode of the chromatography system as illustrated in FIG. 21 is characterized by that the flow distributing valve 301 is in a second position corresponding to the second rotor position shown in FIG. 19. Note that, as for FIG. 20, the mutual positions of the inlets/outlets of valve 301 in FIG. 21 are not drawn identically to that of the embodiment shown in FIG. 19.

Further, in the second operating mode of the system the injection valve 303 is in its LOAD position, the first selection valve 304 is set to connect to another column 313 in-line (another column than was connected during the first operating mode), and the second selection valve 306 is set to connect one of the loops in-line, e.g. loop 315 that holds a sample fraction collected.

With the pump 302 the buffer liquid used is now forced through the flow distributing valve 301 to the second selection valve 306 to bring with it the sample fraction contained in the selected loop 315. The flow returns to the flow distributing valve 301 and from there to the first selection valve 304.

In the second operating mode, a different column 313 than in the first mode may now be connected in-line. Thus, the sample fraction may now be further separated using a different separation technique compared to the previous separation step during the first mode of operation.

Similarly to the first mode of operation, the separated fractions are monitored by the UV sensor 317, and the UV signal is used to control the flow path selection valve 305 to direct the fractions and/or liquid with low sample concentration either to the fraction collector 314, any outlets 319 or back to the flow distributing valve 301.

A fraction that in this way is returned to the flow distributing valve 301 is further directed to the injection valve 302 and may, by acting on this valve, be contained in the capillary loop 311 for further treatment in yet another purification step (performed according to the first mode of operation). Alternatively, liquid may be discharged from the system via the injection valve 302, the flow distributing valve 301 and the outlet 318.

Taking into consideration that a selection valve, such as the first or second selection valves 304, 306, typically includes an internal bypass position it is understood that many such valves can be serially connected. This allows the formation of a system that may hold as many columns and/or loops as desired or as is practically limited by back pressure or band broadening created by interconnecting capillaries.

Figure 22:
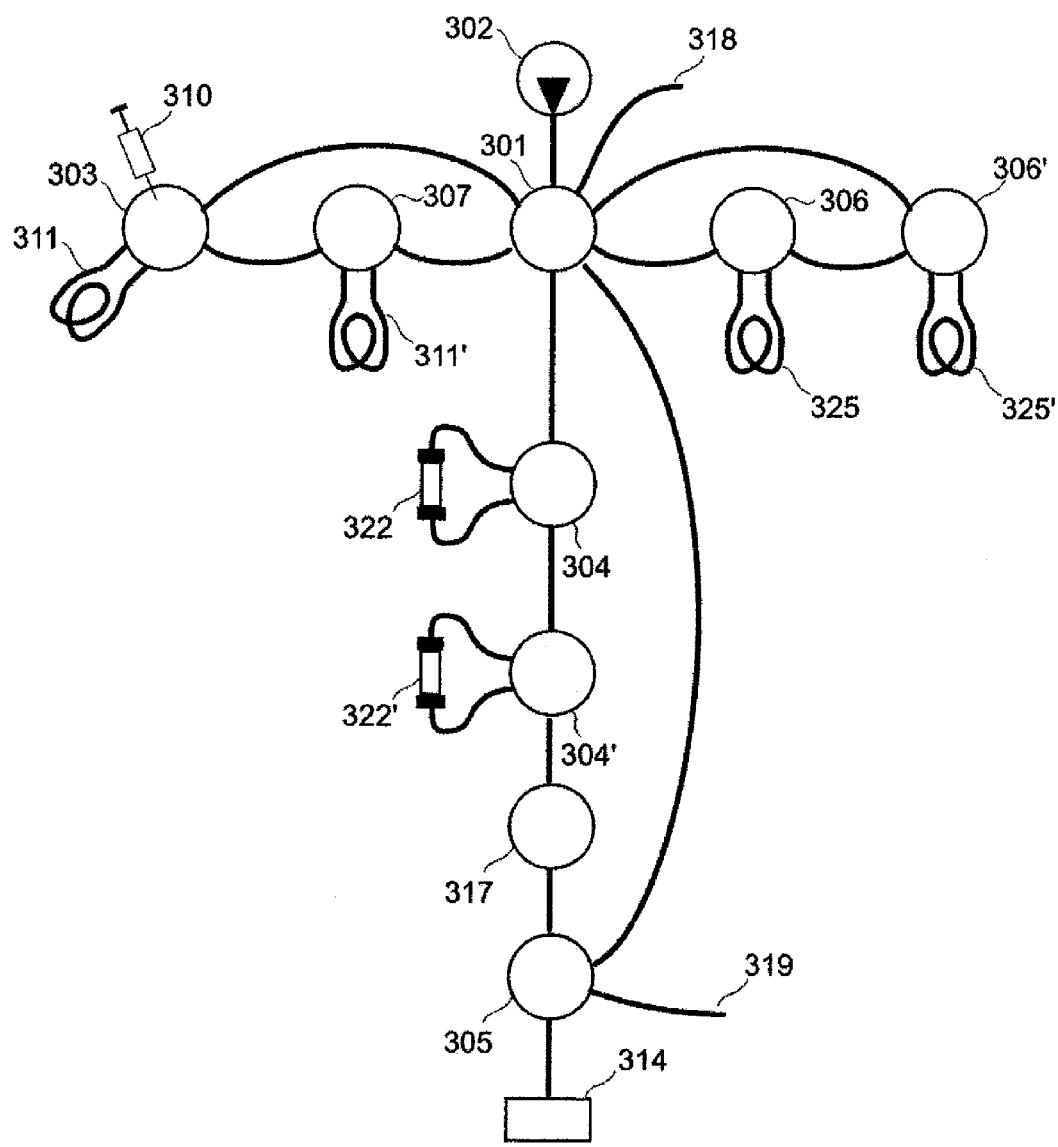
FIG. 22 is a schematic view of an extended chromatography system using a valve according to the invention.

FIG. 22 is a schematic illustration of an example of such a system, extended with two additional loop selection valves 306', 307 and one additional column selection valve 304'.

As compared to the system shown in FIGS. 20 and 21, a third selection valve 306' is placed serially after the second selection valve 306. Although for clarity these valves 306, 306' are shown with one loop 325, 325' each, it should be understood that each valve can have as many loops as it is design for, e.g. five loops each. Thus, the number of fractions that can be stored during a separation run performed in the first mode described above is easily extendable.

Similarly, a fourth selection valve 307 is placed serially after the injection valve 303. For clarity this valve 307 is shown with one loop 311', although it should be understood that it can have as many loops as it is design for, e.g. five loop. Thus, the number of fractions that can be stored initially, or during a separation run performed in the second mode described above is easily extendable.

Finally, as compared to the system shown in FIGS. 20 and 21, a fifth selection valve 304' is placed serially after the first selection valve 304, both these valves being associated with attached chromatography columns 322, 322'. Although for clarity these valves 304, 304' are shown with one column 322, 322' each, it should be understood that each valve can have as many columns as it is design for, e.g. five columns each. Thus, the number of columns useful for different separations of various chromatography techniques performed in the first or second mode described above is easily extendable.

Thus, with a flow distributing valve according to the present invention a flexible automated multi-step multi-dimensional chromatography system can be designed with a minimum number of necessary valves as well as with short interconnecting capillaries, thereby reducing back pressure and band broadening created by the flow path of the system.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A rotary valve (10) for distributing a flow of a fluid, the valve comprising a stator (11) and a rotor (12), wherein said stator (11) comprises at least eight ports protruding into the stator and each port ending in a corresponding orifice on an inner stator face (11a), wherein a first port (21a) ends in a first orifice (21b), a second port (22a) ends in a second orifice (22b), a third port (23a) ends in a third orifice (23b), a fourth port (24a) ends in a fourth orifice (24b), a fifth port (25a) ends in a fifth orifice (25b), a sixth port (26a) ends in a sixth orifice (26b), a seventh port (27a) ends in a seventh orifice (27b) and an eighth port (28a) ends in an eighth orifice (28b), the inner stator face (11a) being a face of the stator making contact in a fluid tight manner with an inner rotor face (12a) of the rotor (12), said inner rotor face (12a) being rotatably movable around a rotational axis (RA) relative to the inner stator face (11a), each one of said stator orifices (21b-28b) being distributed around the rotational axis (RA) at a common radial distance R, further wherein the first, second, third and fourth orifices (21b-24b) form a first group of orifices, each orifice of that group angularly parted from its nearest neighbor by an angle α, the fifth, sixth, seventh and eighth orifices (25b-28b) form a second group of orifices, each orifice of that group angularly parted from its nearest neighbor by the angle α, and the first and the second groups of orifices parted from each other by an angle β in both directions, said inner stator face (11a) further comprising a first stator groove (31) beginning in the fourth orifice (24b) and ending at a position at the radial distance R from the rotary axis (RA) parted with the angle α from the first orifice (21b), and a second stator groove (32) beginning in the fifth orifice (25b) and ending at a position at the radial distance R from the rotary axis (RA) parted with the angle α from the eighth orifice (28b), and wherein said inner rotor face (12a) comprises a first, a second, a third and a fourth rotor groove (41-44) each having both its ends at the radial distance R from the rotary axis (RA), each rotor groove (41-44) extending over the angle α dividing two adjacent orifices of the stator, whereby the first and the second rotor grooves (41, 42) are parted an angle α to form a first set of grooves, and the third and the fourth rotor grooves (43, 44) are parted an angle α to form a second set of grooves, the first set of grooves being placed diametrically opposite the second set of grooves, to allow the stator (11) and the rotor (12) to co-operate in a first rotor position and a second rotor position, whereby the second rotor position is obtained by rotating the rotor an angle of α from the first position, wherein in the first position there is fluid communication between the first port (21a) and the second port (22a) via the first rotor groove (41), between the third port (23a) and the fourth port (24a) via the second rotor groove (42), between the fifth port (25a) and the sixth port (26a) via the third rotor groove (43), and between the seventh port (27a) and the eighth port (28a) via the fourth rotor groove (44), and in the second position there is fluid communication between the first port (21a) and the fourth port (24a) via the first rotor groove (41) and the first stator groove (31), between the second port (22a) and the third port (23a) via the second rotor groove (42), between the fifth port (25a) and the eighth port (28a) via the fourth rotor groove (44) and the second stator groove (32), and between the sixth port (26a) and the seventh port (27a) via the third rotor groove (43).

2. The rotary valve of claim 1, wherein the angle α is 30° and angle β is 90°.

3. The rotary valve of claim 1, wherein the angle α is 36° and angle β is 72°.

4. A chromatography system, comprising the valve of claim 1.

5. The chromatography system of claim 4, further comprising three different components or component groups connected to said valve, wherein the flow direction is kept constant through one of the three components or component groups while the flow direction through the other two component or component groups can be changed.

* * * * *